United States Patent [19]

Takase

[11] Patent Number: 4,957,502
[45] Date of Patent: Sep. 18, 1990

[54] SURGICAL NEEDLE FOR PLASTIC SURGERY OR THE LIKE

[76] Inventor: Haruo Takase, 20-16, 3-chome, Shimoochiai, Shinjuku-ku, Tokyo, Japan

[21] Appl. No.: 396,679

[22] Filed: Aug. 22, 1989

[51] Int. Cl.$^5$ ............................................. A61B 17/00
[52] U.S. Cl. .................................................. 606/223
[58] Field of Search ........................ 606/223; 128/339

[56] References Cited

U.S. PATENT DOCUMENTS 1,592,535 7/1926 Morton ................................ 606/223
1,648,451 11/1927 Fisher .................................. 606/223

FOREIGN PATENT DOCUMENTS 6338441 2/1988 Japan ................................... 606/223
6454515 4/1989 Japan ................................... 606/223

Primary Examiner—Randall L. Green
Assistant Examiner—Jackson: Gary
Attorney, Agent, or Firm—Oblon, Spivak, McClelland, Maier & Neustadt

[57] ABSTRACT

A surgical needle for suturing tissue which is curved so as to comprise a rear part having large curvature, a middle part having small curvature and a leading part having very small curvature, wherein the needle can be easily and smoothly stuck into tissue in suturing operations in cosmetic surgery, plastic surgery and similar surgery can be effectively carried out in safety.

4 Claims, 1 Drawing Sheet

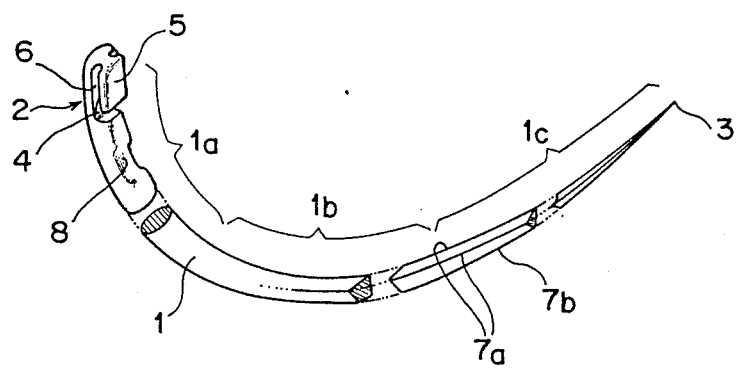
FIG_1
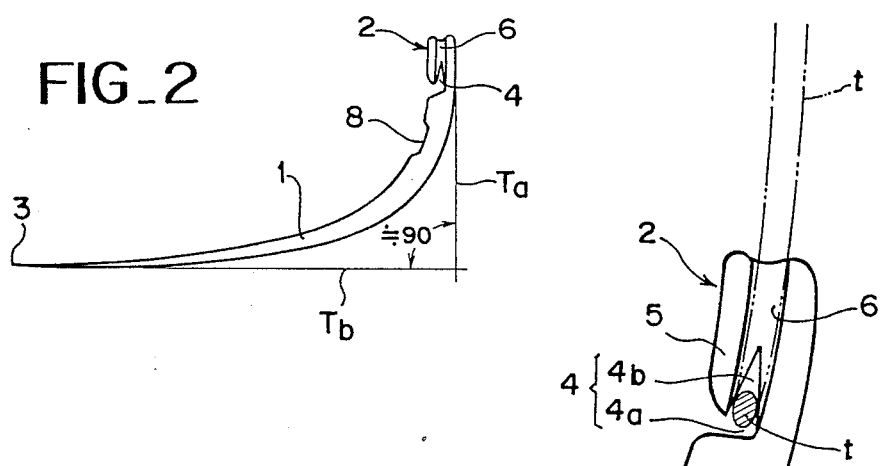
FIG_2
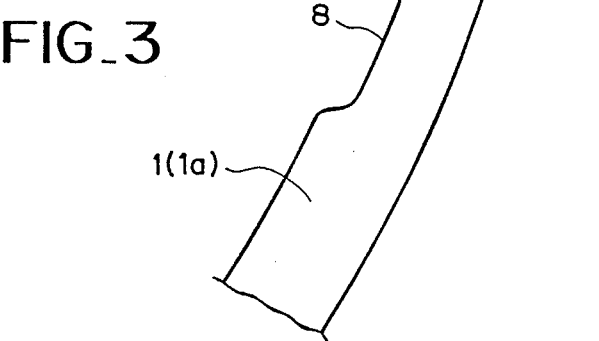
FIG_3

SURGICAL NEEDLE FOR PLASTIC SURGERY OR THE LIKE

BACKGROUND OF THE INVENTION

1. Field of the Invention:

This invention relates to a surgical needle for suturing tissues in cosmetic surgery, plastic surgery and so on, and more particularly is directed to improvements in the curved surgical suturing needle having curvature decreasing gradually from the rear end toward the needle point, which improvements consist in effectively smoothing suturing operation of tissue in plastic surgery or the like.

2. Description of the Prior Art:

For suturing tissue in cosmetic surgery, plastic surgery and so on, a surgical suturing needle which is curved uniformly over the entire length in a substantially semicircular or quadrant shape has generally been used. The inventor of this invention formerly proposed a surgical needle which is curved somewhat sharply in part (Japanese Patent Appln. Pub. Disclosure SHO 63-38441(A)). Also, the inventor proposed a curved surgical needle composed of a leading half portion having a relatively smaller curvature and a rear half portion having a larger curvature (Japanese Utility Model Appln. Public Disclosure SHO 64-54515(A)).

A surgical needle is generally provided in its crown portion (rear end) with a thread hole or notch for allowing a suture thread to pass therethrough or be hooked. Surgical suture of tissue is carried out in such a manner that the suturing needle held at its rear end portion by a needle holder is stuck into the tissue and passed around an incision in the tissue so as to form a spiral suture continuously along the incision. The use of the curved needle shaped in a circular arc makes it possible to effectively suture the tissue in theory.

However, when the surgical needle having a steeply curved leading portion is practically used to suture, it is difficult to stick the needle into the tissue perpendicularly to the skin on account of softness and elasticity of the tissue. When using a surgical needle with a leading portion having a small curvature, the step of pulling out the needle stuck through the tissue becomes much harder. Thus, it would appear that the surgical needle comprising the leading half portion having small curvature and the rear half portion having large curvature as proposed by the aforenoted Japanese Utility Model Application Public Disclosure SHO 64-54515(A) is the most acceptable for surgically suturing purpose.

The surgical needle is generally provided in its crown portion (rear end portion) with a thread hole. The thread hole provided is typically formed by longitudinally cutting the crown portion into opposite pieces and bringing the opposite pieces into springy contact with each other. Though a suture thread can readily be inserted with a single operation into the thread hole thus formed, it entails a structural drawback in that the suture thread inserted in the thread hole easily comes out from the thread hole in surgical operation. Besides, since the suture thread inserted in the thread hole is folded backward at the thread hole, the thread is protrudes laterally from either side surface of the needle. The laterally protruding portions of the thread would injure excessively the tissue and thin blood vessels in needling, thereby to involving profuse bleeding, subcutaneous hematoma or the like. As a result, convalescence will be lengthened.

SUMMARY OF THE INVENTION

An object of this invention is to provide a surgical needle suitable for suturing tissue, which is curved over the entire length thereof at such a curvature that the needle can be easily and smoothly stuck into tissue for suturing without changing the manner of holding a needle holder by which the needle is held in suturing, so that suturing operations in cosmetic surgery, plastic surgery and so on can be effectively carried out.

Another object of this invention is to provide a surgical needle for suturing tissue, having a thread hole formed in the rear end portion of the needle, which allows a suture thread to be readily inserted thereinto and can secure steady the thread inserted in the hole so that the tissue is little injured by the suture thread retained by the needle in a two folded state when the needle is stuck through the tissue.

To attain the objects mentioned above, the surgical needle for suturing tissue according to this invention comprises a rear part having a large curvature and provided at its rear end portion with thread retaining means, a middle part having small curvature and a leading part having very small curvature, wherein the needle is curved over the entire length thereof so that the rear part is at substantially right angles to the leading part.

Since the curvature of the leading part of the surgical needle is relatively smaller, the needle can be easily and smoothly stuck into the tissue in not only the perpendicular direction, but also all directions relative to the skin without changing the manner of holding a needle holder by which the needle is held for suturing. Besides, according to this invention, suturing operation can be effectively carried out while coping with various suturing conditions such as softness and elasticity of the tissue to be sutured.

The thread retaining means at the rear end portion of the needle consists of a side notch opening laterally in one side of the needle and a longitudinal slot extending backward from the side notch, so that a substantially L-shaped thread hole is formed by the side notch and longitudinal slot. The longitudinal slot is formed in the shape of the letter "V" so as to prevent the suture thread retained in the thread hole from coming out.

By forming a thread groove extending backward from the longitudinal slot in either side surface of the needle, two-folded thread parts of the suture thread which is inserted through the thread hole and folded backward are fitted in the thread grooves. Consequently, the two-folded thread parts of the suture thread are not protruded sidewards, with the result that the tissue is little injured by the suture thread retained by the needle.

BRIEF DESCRIPTION OF THE DRAWINGS

The other objects and features of the present invention will now be explained in detail with reference to the accompanying drawings, wherein:

FIG. 1 is a partially sectioned perspective view showing one preferred embodiment of the present invention, FIG. 2 is a side view of the same, and FIG. 3 is an enlarged detail of the same.

DESCRIPTION OF THE PREFERRED EMBODIMENT

As illustrated in the attached drawings by way of example, the surgical needle for suturing tissue according to this invention comprises a needle body 1 provided at the rear end portion 1a with thread retaining means 2 for allowing a suture thread t to be inserted therein and retained. The needle body 1 is curved over the entire length thereof so as to gradually decrease the curvature of the curved needle from the rear end portion 1a toward a needle point 3. That is, the needle body 1 is composed of the aforesaid rear part 1a having large curvature, a middle part 1b having small curvature and a leading part 1c having small curvature. Preferably, the needle body 1 is curved so that the rear part 1a having a large curvature is at substantially a right angle to the leading part 1c having very small curvature.

To be more specific, the angular relation between the rear part 1a and the leading part 1c is so determined that tangent line Ta to the rear part 1a meets at substantially right angles to a tangent line Tb to the leading part 1c. Though the surgical needle is, in this embodiment, curved over the, entire length thereof as mentioned above, the one-fifth of the side or length of the rear part 1a may be substantially straightened.

According to this invention, since the surgical needle is curved so as to gradually decrease its curvature toward the needle point 3, the needle can be easily and smoothly stuck into tissue and then, pulled out from the tissue after being thrust around an incision in the tissue. Furthermore, since the rear part 1a having large curvature is at substantially right angles to the leading part 1c having a very small curvature, sticking of the needle into the tissue can be steadily carried out without changing the manner of holding a needle holder (not shown) by which the needle is held in suturing.

The thread retaining means 2 provided at the rear part 1a of the needle comprises a substantially L-shaped thread hole 4 composed of a side notch 4a opening laterally in one side of the needle body 1 and a longitudinal slot 4b extending backward from the side notch 4a. The substantially L-shaped thread hole 4 is defined by a spring piece 5 having adequate elasticity. The longitudinal slot 4b decreases its inner width toward the rear end (needle crown) so as to assume a substantially V-shape. The space between the pointed end of the spring piece 5 and the opposite face to the spring piece 5 on the needle body 1 is made somewhat narrower than the diameter of the suture thread t. Therefore upon once passing the suture thread t through the side notch 4a, the suture thread t cannot easily go backward. Besides, since the inner width of the substantially V-shaped longitudinal slot 4b is decreased toward the rear end of the needle, the suture thread t cannot easily come out owing to the wedge effect of the substantially V-shaped longitudinal slot 4b and the elastic force of the spring piece 5. Thus, the aforementioned thread retaining means 2 allows easy passing and steady holding of the suture thread through and in the thread hole 4.

In addition, the rear part 1a of the needle body 1 has thread grooves 6 formed in the side surfaces of the needle body 1 and extending backward from the longitudinal slot 4b. The thread grooves 6 each have a width substantially equal to or somewhat larger than the diameter of the suture thread t. Therefore, two-folded thread parts of the suture thread which is inserted through the thread hole 4 and folded backward are fitted in the thread grooves 6. Consequently, the two-folded thread parts of the suture thread t do not protruded sidewards from the thread grooves 6, with the result that the tissue is little injured by the suture thread retained by the needle.

The needle body 1 is provided with cutting edges 7a, 7b extending from the middle part 1b to the needle point 3. The cutting edges 7a protrude sidewards and the cutting edge 7b protrudes downward. Though the needle body 1 has a section shaped in an isosceles triangle as illustrated, the section of the needle body 1 should not be understood as limitative. The rear part 1a has a section shaped in a circle or ellipse.

In the drawings, reference numeral 8 denotes a holding portion which is held by a needle holder (not shown) in suturing operation. In this embodiment, the holding portion 8 is formed by partly in denting the rear part 1a, but it is not necessarily in dented. For example, the inner surface and/or outer surface of the curved needle body 1 may be made flat so as to allow the needle to be easily and steady seized by the needle holder.

As is clear from the foregoing, in accordance with the present invention, it is possible to provide a surgical needle capable of being easily and smoothly stuck into tissue in a direction perpendicular to the skin or a desired direction and effectively carrying out suturing operation in cosmetic surgery, plastic surgery and so on without changing the manner of holding a needle holder by which the needle is held in suturing because the needle is curved over the entire length thereof so as to gradually decrease the curvature of the curved needle from the rear end portion toward the needle point. Furthermore, since the thread hole formed in the rear end portion of the needle is formed so as to be in a substantially L-shape, a suture thread can be readily inserted thereinto and reliably secured in the thread hole. Besides, the thread grooves extending backward from the longitudinal slot are formed in the rear end portion of the needle and the two-folded thread parts of the suture thread which is inserted through the thread hole and folded backward are fitted in the thread grooves, whereby the tissue is little injured by the suture thread retained by the needle.

As can be readily appreciated, it is possible to deviate from the above embodiment of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A surgical needle for suturing tissue, which comprises:
    a curved needle body which includes a rear part having a large curvature and provided at its rear end portion with thread retaining means, a middle part having a small curvature and a leading part having a very small curvature wherein substantially one-fifth of the length of said rear part of said needle is at a substantially right angle to a tangent line with respect to said leading part.

2. A surgical needle according to claim 1, wherein said thread retaining means comprises a substantially L-shaped thread hole which includes a side notch opening laterally on one side of said needle body and a substantially V-shaped longitudinal slot extending rearward from said side notch.

3. A surgical needle according to claim 2, wherein said rear part of said needle body has thread grooves extending backward said longitudinal slot.

4. A surgical needle according to claim 1, wherein said needle body is provided with cutting edges extending from said middle part to the leading part.

* * * * *